United States Patent
Grant et al.

(10) Patent No.: US 12,236,920 B2
(45) Date of Patent: Feb. 25, 2025

(54) AUGMENTED REALITY SESSIONS RESPONSIVE TO EYE BEHAVIOR

(71) Applicant: International Business Machines Corporation, Armonk, NY (US)

(72) Inventors: Robert Huntington Grant, Marietta, GA (US); Juan C. Lopez, Tampa, FL (US); Alexander DeFarlo, Armonk, NY (US); Zachary A. Silverstein, Jacksonville, FL (US)

(73) Assignee: International Business Machines Corporation, Armonk, NY (US)

( * ) Notice: Subject to any disclaimer, the term of this patent is extended or adjusted under 35 U.S.C. 154(b) by 928 days.

(21) Appl. No.: 16/939,635

(22) Filed: Jul. 27, 2020

(65) Prior Publication Data

US 2022/0028356 A1 Jan. 27, 2022

(51) Int. Cl.
*G09G 5/36* (2006.01)
*A61B 5/16* (2006.01)
(Continued)

(52) U.S. Cl.
CPC ............ *G09G 5/36* (2013.01); *A61B 5/163* (2017.08); *A61B 5/165* (2013.01); *G06K 9/00604* (2013.01); *A61B 3/112* (2013.01); *A61B 3/113* (2013.01); *A61B 2090/365* (2016.02); *A61B 2505/09* (2013.01); *G09G 2354/00* (2013.01)

(58) Field of Classification Search
CPC ...... G09G 5/36; G09G 2354/00; A61B 5/163; A61B 5/165; A61B 2505/09; A61B 3/113; A61B 2090/365; A61B 3/112; G06K 9/00604
See application file for complete search history.

(56) References Cited

U.S. PATENT DOCUMENTS

| | | |
|---|---|---|
| 6,231,187 B1 | 5/2001 | Munoz et al. |
| 9,823,737 B2 | 11/2017 | Mazed et al. |

(Continued)

FOREIGN PATENT DOCUMENTS

WO 2017186721 A1 11/2017

OTHER PUBLICATIONS

Orlosky et al., "Emulation of Physician Tasks in Eye-Tracked Virtual Reality for Remote Diagnosis of Neurodegenerative Disease," in IEEE Transactions on Visualization and Computer Graphics, vol. 23, No. 4, Apr. 2017, 10 pages.

(Continued)

*Primary Examiner* — Maurice L. McDowell, Jr.
(74) *Attorney, Agent, or Firm* — Timothy J. Singeton

(57) ABSTRACT

A method, system, and computer program product for generating augmented reality sessions based on eye behavior of a user is provided. The method detects a set of eye characteristics of a user. In response to detecting the set of eye characteristics, presentation of an augmented reality session is initiated using an augmented reality device. The method detects a change to at least one eye characteristic of the set of eye characteristics of the user. In response to detecting the change, the method determines the change to the at least one eye characteristic indicates a reduced cognitive state of the user. The augmented reality state being presented to the user is modified in response to determining the change indicates the reduced cognitive state.

14 Claims, 7 Drawing Sheets

(51) Int. Cl.
  *G06K 9/00* (2022.01)
  *A61B 3/11* (2006.01)
  *A61B 3/113* (2006.01)
  *A61B 90/00* (2016.01)

(56) References Cited

U.S. PATENT DOCUMENTS

| | | |
|---|---|---|
| 10,332,315 B2 | 6/2019 | Samec et al. |
| 2004/0181168 A1 | 9/2004 | Plant et al. |
| 2013/0278899 A1 | 10/2013 | Waldorf et al. |
| 2013/0321772 A1* | 12/2013 | White .................... A61B 3/113 351/209 |
| 2014/0255888 A1* | 9/2014 | Stack .................... A61B 3/113 434/236 |
| 2015/0097772 A1* | 4/2015 | Starner .................. G06F 3/013 345/158 |
| 2016/0007921 A1 | 1/2016 | Galea et al. |
| 2016/0085302 A1* | 3/2016 | Publicover .......... G02B 27/017 345/633 |
| 2016/0229412 A1* | 8/2016 | Gordon ............. G06K 9/00845 |
| 2016/0262608 A1 | 9/2016 | Krueger |
| 2017/0135577 A1* | 5/2017 | Komogortsev ...... A61B 5/7282 |
| 2017/0365101 A1* | 12/2017 | Samec .................. A61B 5/163 |
| 2019/0009049 A1 | 1/2019 | Candy |
| 2019/0246969 A1* | 8/2019 | Thomas ................ G06T 7/0012 |
| 2019/0287309 A1 | 9/2019 | Samec et al. |
| 2019/0307350 A1 | 10/2019 | Sridhar et al. |
| 2019/0307384 A1* | 10/2019 | Baeuerle ............. A61B 5/1123 |
| 2020/0029802 A1* | 1/2020 | Lane ....................... A61B 3/02 |
| 2020/0187860 A1* | 6/2020 | Myslinski ............ A61B 5/4839 |

OTHER PUBLICATIONS

Molitor et al., "Eye Movements in Alzheimer's Disease", J Alzheimers Dis. 2015 ; 44(1), doi:10.3233/JAD-141173, 18 pages, available in PMC Mar. 1, 2017. https://www.ncbi.nlm.nih.gov/pmc/articles/PMC5332166/.

IBM Research, IoT and Wearables, printed Feb. 21, 2020, 6 pages. https://www.research.ibm.com/haifa/dept/services/wearable.shtml.

"Activities at Home", Alzheimer's Association, © 2019 Alzheimer's Association, Sep. 2019, 12 pages.

Schroder et al., "Deep Learning for Action Recognition in Augmented Reality Assistance Systems", SIGGRAPH '17 Posters, Los Angeles, CA, DOI: 10.1145/3102163.3102191, 2 pages.

Mell et al., "The NIST Definition of Cloud Computing", Recommendations of the National Institute of Standards and Technology, Special Publication 800-145, Sep. 2011, 7 pages.

* cited by examiner

… (1)

AUGMENTED REALITY SESSIONS RESPONSIVE TO EYE BEHAVIOR

BACKGROUND

Some rehabilitation therapies are used after an Alzheimer's diagnosis. Rehabilitation therapies may be complicated by memory issues. Often, repetitive activities are suggested to patients. Performing these repetitive activities may become a part of rehabilitation therapies for patients.

SUMMARY

According to an embodiment described herein, a computer-implemented method for generating augmented reality sessions based on eye behavior of a user is provided. The method detects a set of eye characteristics of a user. In response to detecting the set of eye characteristics, presentation of an augmented reality session is initiated using an augmented reality device. The method detects a change to at least one eye characteristic of the set of eye characteristics of the user. In response to detecting the change, the method determines the change to the at least one eye characteristic indicates a reduced cognitive state of the user. The augmented reality state being presented to the user is modified in response to determining the change indicates the reduced cognitive state.

According to an embodiment described herein, a system for generating augmented reality sessions based on eye behavior of a user is provided. The system includes one or more processors and a computer-readable storage medium, coupled to the one or more processors, storing program instructions that, when executed by the one or more processors, cause the one or more processors to perform operations. The operations detect a set of eye characteristics of a user. In response to detecting the set of eye characteristics, presentation of an augmented reality session is initiated using an augmented reality device. The operations detect a change to at least one eye characteristic of the set of eye characteristics of the user. In response to detecting the change, the operations determine the change to the at least one eye characteristic indicates a reduced cognitive state of the user. The augmented reality state being presented to the user is modified in response to determining the change indicates the reduced cognitive state.

According to an embodiment described herein a computer program product for generating augmented reality sessions based on eye behavior of a user is provided. The computer program product includes a computer readable storage medium having program instructions embodied therewith, the program instructions being executable by one or more processors to cause the one or more processors to detect a set of eye characteristics of a user. In response to detecting the set of eye characteristics, presentation of an augmented reality session is initiated using an augmented reality device. The computer program product detects a change to at least one eye characteristic of the set of eye characteristics of the user. In response to detecting the change, the computer program product determines the change to the at least one eye characteristic indicates a reduced cognitive state of the user. The augmented reality state being presented to the user is modified in response to determining the change indicates the reduced cognitive state.

DETAILED DESCRIPTION

Figure 1:
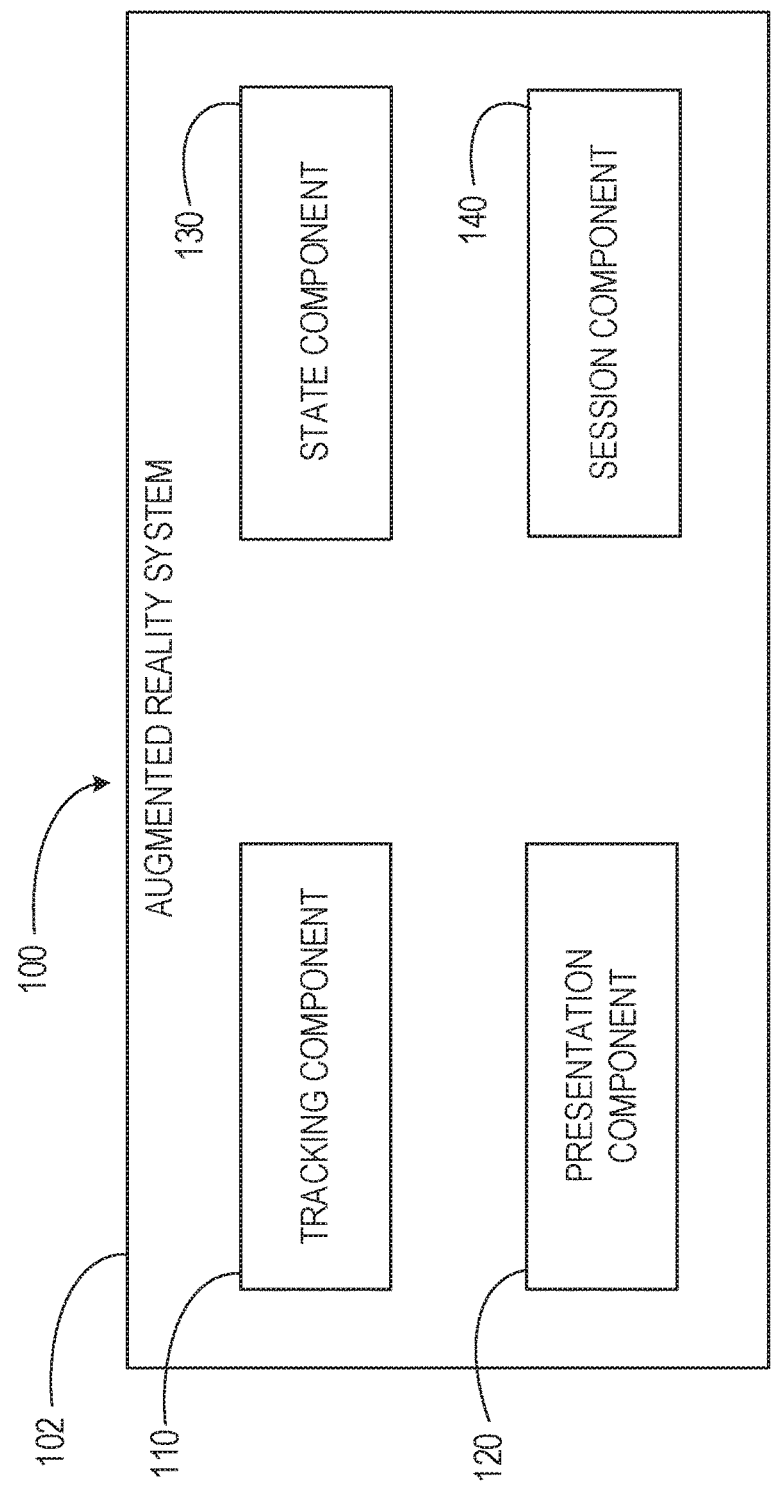
FIG. 1 depicts a block diagram of a computing environment for implementing concepts and computer-based methods, according to at least one embodiment.

The present disclosure relates generally to methods for dynamically generating and altering augmented reality presentations. More particularly, but not exclusively, embodiments of the present disclosure relate to a computer-implemented method for generating augmented reality sessions based on eye behavior of a user. The present disclosure relates further to a related system for generating and altering augmented reality presentations, and a computer program product for operating such a system.

Alzheimer's patients suffer from memory issues, among other ailments. Rehabilitation for Alzheimer's patients may involve repetitive activities to stimulate memory. Abnormal eye behaviors may indicate decreased attentiveness or cognition in Alzheimer's patients during rehabilitation. Monitoring of such behaviors may enable trained rehabilitation staff to increase efficacy of treatments. Rehabilitation may be hampered due to inconsistent rehabilitation staffing and appointment times. Alzheimer's patients may benefit from more consistent rehabilitation efforts and staff.

Augmented reality interfaces present user interface elements within a display screen in a manner which augments a real-world view displayed on the display screen. Augmented reality interfaces may be presented on mobile computing device displays such as those on mobile phones, glasses, and tablets. Augmented reality devices may enable display of interactive elements in real-world environments.

Embodiments of the present disclosure provide augmented reality interfaces configured to provide rehabilitation and therapy activities for patients encountering memory issues. Some embodiments of the present disclosure enable rehabilitation staff or administrators to provide a venue for engaging in repetitive activities to facilitate rehabilitation therapies. Embodiments of the present disclosure provide automated monitoring of eye behavior and characteristics to aid in tracking or monitoring of patient attentiveness and cognition. Some embodiments of the present disclosure provide augmented reality interfaces which dynamically respond to monitored eye behavior. Such embodiments enable modification of augmented reality sessions to boost or maintain patient attentiveness and cognition during a therapy or rehabilitation session. Modifications to the augmented reality sessions may be based on a combination of eye behavior and previously successful augmented reality sessions.

Some embodiments of the concepts described herein may take the form of a system or a computer program product. For example, a computer program product may store program instructions that, when executed by one or more processors of a computing system, cause the computing system to perform operations described above with respect to the computer implemented method. By way of further example, the system may comprise components, such as processors and computer readable storage media. The computer readable storage media may interact with other components of the system to cause the system to execute program instructions comprising operations of the computer implemented method, described herein. For the purpose of this description, a computer-usable or computer-readable medium may be any apparatus that may contain means for storing, communicating, propagating, or transporting the program for use, by, or in connection with, the instruction execution system, apparatus, or device.

Referring now to FIG. 1, a block diagram of an example computing environment 100 is shown. The present disclosure may be implemented within the example computing environment 100. In some embodiments, the computing environment 100 may be included within or embodied by a computer system, described below. The computing environment 100 may include an augmented reality system 102. The augmented reality system 102 may comprise a tracking component 110, a presentation component 120, a state component 130, and a session component 140. The tracking component 110 tracks eye movement and location for a user engaging with an augmented reality device. The presentation component 120 presents an augmented reality user interface to the user responsive to eye characteristics of the user. The state component 130 determines changes to eye characteristics and cognitive states of the user during augmented reality sessions. The session component 140 monitors augmented reality sessions and provides information from previous augmented reality sessions to be presented within a current augmented reality session. Although described with distinct components, it should be understood that, in at least some embodiments, components may be combined or divided, or additional components may be added, without departing from the scope of the present disclosure.

Figure 2:
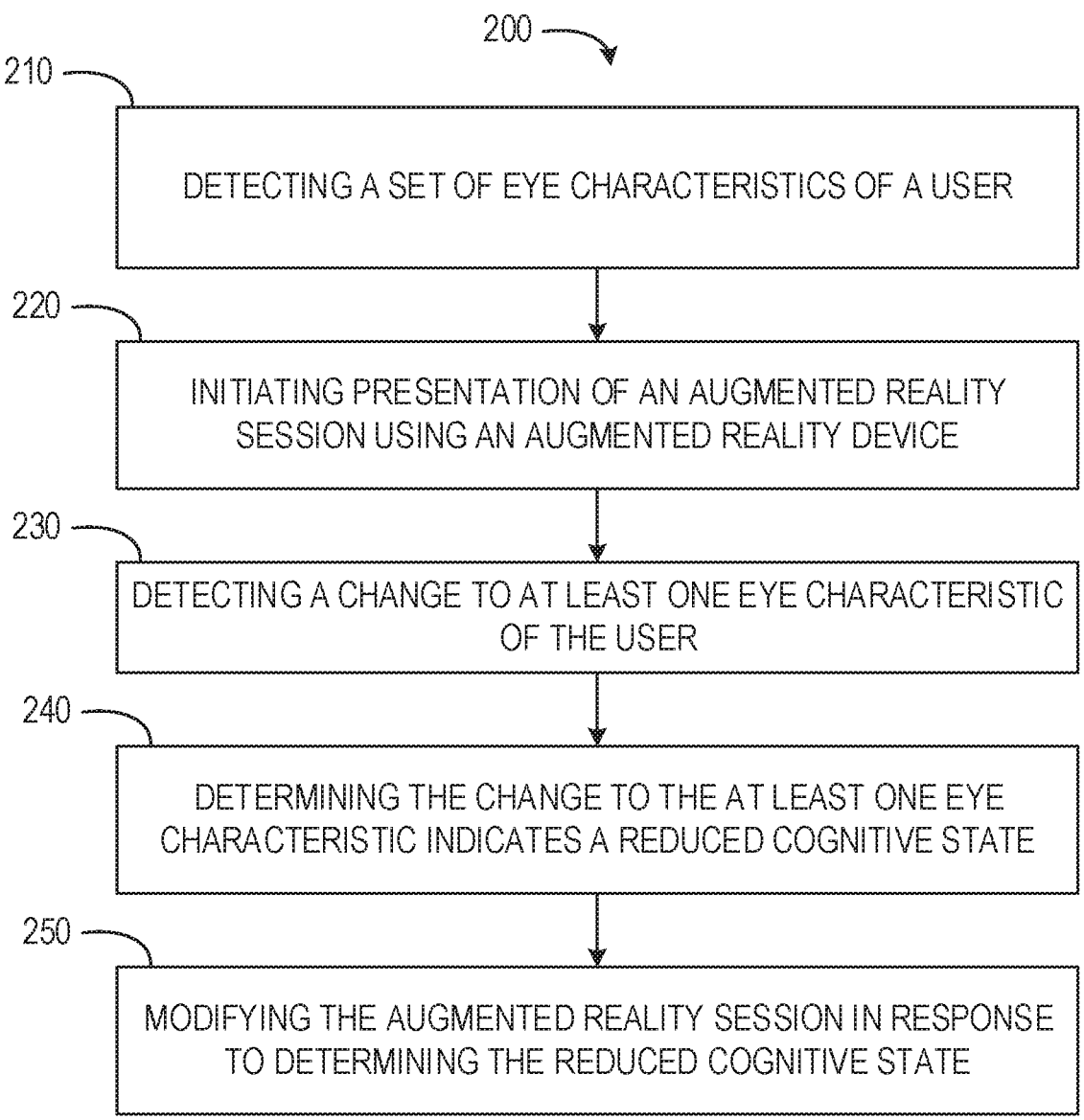
FIG. 2 depicts a flow diagram of a computer-implemented method for generating augmented reality sessions based on eye behavior of a user, according to at least one embodiment.

Referring now to FIG. 2, a flow diagram of a computer-implemented method 200 is shown. The computer-implemented method 200 is a method for generating augmented reality sessions based on abnormal eye behavior of a user. In some embodiments, the computer-implemented method 200 may be performed by one or more components of the computing environment 100, as described in more detail below.

At operation 210, the tracking component 110 detects a set of eye characteristics of a user. The tracking component 110 may detect the eye characteristics using an image capture device of an augmented reality device. The set of eye characteristics may include eye movements, duration of eye movements, frequency of eye movements, eye movement changes over time, pupillary changes, duration of pupillary changes, frequency of pupillary changes, pupillary movement over time, combinations thereof, and any other and relevant characteristics of the eye indicating or representative of a level of attentiveness or cognition. In some embodiments, eye movements include saccades, smooth pursuit movements, vergence movements, and vestibulo-ocular movements. Saccades may be rapid movements of the eyes which change a point of fixation of the eyes. Smooth pursuit movements are relatively slower tracking movements of the eyes which maintain focus on a moving stimulus. Vergence movements may align a focal point of the eyes or vision with objects at varying distances from the eye. Vestibulo-ocular movements may stabilize eyes to compensate for external movements, such as movements of the head or body.

In some embodiments, the augmented reality device comprises a frame and a set of lenses. The frame may be coupled to the set of lenses. In some embodiments, the augmented reality device is configured as a set of glasses. The frame may be configured to be positioned on a face of a user, such that at least one lens of the set of lenses is positioned in line with an eye of the user. In some embodiments, the augmented reality device also comprises a set of image capture devices. The set of image capture devices may be coupled to one or more of the frame and the set of lenses.

In some embodiments, at least one image capture device of the set of image capture devices is positioned on an interior of the frame. The at least one image capture device (e.g., a front facing camera) may be positioned at an orientation such that the eye of the user is in a field of view of the at least one image capture device. In some embodiments, the at least one image capture device is an interior set of image capture devices. The interior set of image capture devices may be positioned in an orientation sufficient to capture each eye of the user in a field of view of at least one image capture device of the interior set of image capture devices.

In some embodiments, at least one image capture device of the set of image capture devices is positioned on an exterior of the frame. The at least one image capture device (e.g., a rear facing camera or first image capture device) may be positioned at an orientation such that the at least one image capture device has a field of view which encompasses or includes at least a portion of a field of view of the user while the user is wearing the augmented reality device. In some embodiments, the at least one image capture device acts as a rear facing camera for the augmented reality device. The rear facing camera may act as an input for the augmented reality device, enabling recognition of objects, people, and context surrounding the user and the augmented reality device. For example, the rear facing camera may be used to recognize a session administrator of an augmented reality session for the user, as described in more detail below.

The set of lenses may be configured to display a user interface for the user. The user interface may be an augmented reality user interface. In some embodiments, when the augmented reality user interface is displayed on the set of lenses, a user wearing the augmented reality device sees in a normal field of view through the lenses. Interface elements presented within the augmented reality user interface on the set of lenses may be seen by the user, within the field of view, as images positioned in a real-world environment. For example, a user interface element depicting a shape may be displayed within the set of lenses as a ball suspended in a line of sight of the user. The interface elements may be opaque, translucent, or any other suitably visible depiction. Where the augmented reality device has one or more interior image capture devices, the set of lenses may be configured such that the user may see through the lenses while the eyes of the user are in a field of view of the one or more interior image capture devices.

The tracking component 110 may detect the set of eye characteristics as an initial set of characteristics at a single point in time or an initial set of characteristics over a specified period of time. For example, the tracking component 110 may cooperate with a front facing image capture device of the augmented reality device to capture a set of frames of the eyes of the user. The set of frames may be captured as individual images or as a set of frames within a video stream. The tracking component 110 may use object detection and object recognition operations to detect the set of eye characteristics within the set of frames. The tracking component 110 may detect the set of eye characteristics by identifying locations of an iris and a pupil for each eye of the user. The tracking component 110 may measure an iris location for the iris of each eye within the set of frames. The tracking component 110 may also measure a pupil location for the pupil of each eye of the user. The tracking component 110 may then measure aspects of the eyes. The aspects of the eyes may include one or more of an area, a circumference, a radius, and a diameter of each iris and each pupil. Where the set of frames are captured within a video stream, the tracking component 110 may measure a plurality of locations and a plurality of aspects. The plurality of locations may include an iris location and a pupil location for each frame of the set of frames. The plurality of aspects may include aspects measured for each frame of the set of frames. In this manner, the tracking component 110 may determine a change in time for the eye characteristics within the set of frames. The tracking component 110 may establish a baseline for the eye characteristics of the user based on the locations and aspects measured within the set of frames.

The tracking component 110, in operation 210, may generate a baseline for the set of eye characteristics. The baseline may be determined based on an initial location of the iris and the pupil and a size of the pupil within the set of frames captured for determining the set of eye characteristics. The initial location may be a location within one or more frames of the set of frames described in operation 210. The initial location may be a set of coordinates, a set of pixels, or any other suitable location or set of locations within the set of frames. As the set of eye characteristics are determined, variations in the location of the iris and pupil as well as the size of the pupil may be determined to generate a range of locations for the iris and pupil and a range of sizes for the pupil. Further, the tracking component 110 may generate a baseline for eye movement for the set of eye characteristics. The tracking component 110 may generate the baseline by determining a range of eye movement for saccades, smooth pursuit movements, vergence movements, and vestibulo-ocular movements within the set of frames described in operation 210.

At operation 220, the presentation component 120 initiates presentation of an augmented reality session using the augmented reality device. The presentation component 120 may initiate the presentation in response to detecting the set of eye characteristics. The augmented reality session may be part of a repetitive task therapy for Alzheimer patients. The augmented reality session may be associated with metadata tags describing a therapeutic lesson and goals therefor. The augmented reality session may present visualization, user interface elements, reminders, prompts, or reinforcement indicators enabling a patient to perform repetitive therapy tasks or practice cognitive skills in a monitored session.

At operation 230, the tracking component 110 detects a change to at least one eye characteristic of the set of eye characteristics of the user. After the tracking component 110 detects the set of eye characteristics and the presentation component 120 initiates presentation of the augmented reality session, the tracking component 110 monitors one or more of the eyes of the user during the course of the augmented reality session. The tracking component 110 monitors the one or more eyes to track eye focus, eye movements, and other aspects of the eyes to detect changes in focus of the user, cognitive state, attentiveness, and other relevant factors contributing to successful completion of the augmented reality session.

In some embodiments, the tracking component 110 detects the change to the at least one eye characteristic by comparing current locations and measured aspects of the eyes with the locations and measured aspects of the eyes forming the set of eye characteristics. While monitoring the eyes of the user during the augmented reality session, the tracking component 110 intermittently or continuously measures locations of the iris and pupil of one or more of the eyes. The tracking component 110 also measures eye movement of the at least one eye. In some embodiments, the tracking component 110 measures the locations, the aspects, and the eye movement based on or relative to the locations, aspects, and eye movement detected in operation 210. In some embodiments, the tracking component 110 measures the locations, the aspects, and the eye movement independently of the set of eye characteristics.

In some embodiments, the tracking component 110 detects the change to the at least one eye characteristics by comparing one or more of positions, measurements, and eye movements as the tracking component 110 monitors the eye during the augmented reality session. The tracking component 110 may compare the positions, measurements, and eye movements, during the augmented reality session, to a baseline for the positions, measurements, and eye movements, determined for the set of eye characteristics during operation 210. In some embodiments, the tracking component 110 detects the change to the at least one eye characteristic by determining an eye characteristic, being monitored during the augmented reality session, exceeds a range established for the set of eye characteristics. In some embodiments, the tracking component 110 generates a notification of the change in the at least one eye characteristic in response to the eye characteristic exceeding the established baseline range.

At operation 240, the state component 130 determines the change to the at least one eye characteristic indicates a reduced cognitive state of the user. The state component 130 may determine the change in state in response to the tracking component 110 detecting the change. The state component 130 may receive the notification from the tracking component 110. The notification may indicate the at least one eye characteristic which changed. The notification may also indicate a magnitude of the change, an amount of the change, or an amount by which the at least one eye characteristic exceeded the baseline range.

In some embodiments, the state component 130 determines a standard cognitive state for the user. The standard cognitive state is associated with a set of characteristics thresholds for the user. In some instances, the set of characteristics thresholds are the baseline range determined for the set of eye characteristics. The set of characteristic thresholds are determined based on a historical baseline range for the user, determined across multiple augmented reality sessions. The multiple augmented reality sessions may be augmented reality sessions in which the user has previously participated. The standard cognitive state may include a change of the standard cognitive state. The change of the standard cognitive state may indicate decline or improvement of the user's cognitive state across the multiple augmented reality sessions. In some embodiments, the standard cognitive state is determined for a plurality of users, including an average range of eye movement and pupil measurements. The average range of eye movement and pupil measurements may be augmented with historical measurements for eye movement and pupil size of the user to tailor an average range of eye movement and pupil measurements to that of the user. The average range may be incorporated in instances where no historical measurements exist for the user.

The state component 130 accesses the standard cognitive state for the user. The state component 130 may access the standard cognitive state in response to detecting the change to the at least one eye characteristic. The state component 130 may access the standard cognitive state from a user repository. The user repository may be a data structure containing information about augmented reality sessions of the user. The user repository may be stored on the augmented reality device. In some embodiments, the user repository is contained on a computing device associated with an administrator of the augmented reality session. The user repository may also be stored on any computing device or resource capable of being accessed by the augmented reality device.

The state component 130 determines the change to the at least one eye characteristic exceeds a characteristic threshold of the set of characteristic thresholds. The set of characteristic thresholds may be associated with the standard cognitive state for the user. In some embodiments, each characteristic threshold of the set of characteristic thresholds are associated with a range or measurement of the eye for the standard cognitive state. Where a characteristic threshold, such as a range of eye movement, is exceeded by the change to the at least one eye characteristic, the change may indicate a decrease in attention or a cognitive state of the user. The state component 130 may compare the change to the at least one eye characteristic and the characteristic threshold by calculating a difference between their respective values.

At operation 250, the session component 140 modifies the augmented reality session being presented to the user. The session component 140 may modify the augmented reality session in response to determining the change indicates the reduced cognitive state. The augmented reality session may modify the augmented reality session by determining a context of the current augmented reality session. The context of the augmented reality session may be included in metadata indicating one or more of a subject of the augmented reality session, a content of the augmented reality session, an activity of the augmented reality session, an administrator of the augmented reality session, combinations thereof, or any other suitable contextual information. The session component 140 may modify the current augmented reality session by retrieving a historical context for a historical augmented reality session which matches the context of the current augmented reality session. The session component 140 determines a most successful historical augmented reality session (e.g., a selected session). The relative success of historical augmented reality sessions may be determined based on a session rank. The session rank may be determined by values indicating one or more of a number of completed session goals, a difficulty of completed session goals, a time spent in a standard cognitive state during a given session, therapist feedback, combinations thereof, or any other suitable and relevant success metrics. The session component 140 may retrieve information about the selected session and incorporates elements of the selected session into the current augmented reality session. The elements incorporated into the current augmented reality session may include visual aspects, activities, audio aspects, or any other suitable elements or components of the selected session.

In some embodiments, the session component 140 stores session characteristics of the augmented reality session and eye characteristics of the user in the session log. The session component 140 may store the session characteristics and eye characteristics in response to completing the augmented reality session. The session component 140 may store the session characteristics and eye characteristics of each completed or attempted augmented reality session in the session log. The session log may be anonymized to remove any identifying information about the user. The user may be assigned login credentials or an anonymized identification number for a session log associated with that user. The session characteristics and eye characteristics may be fed as input into a machine learning model to tailor later augmented reality sessions for the user.

Figure 3:
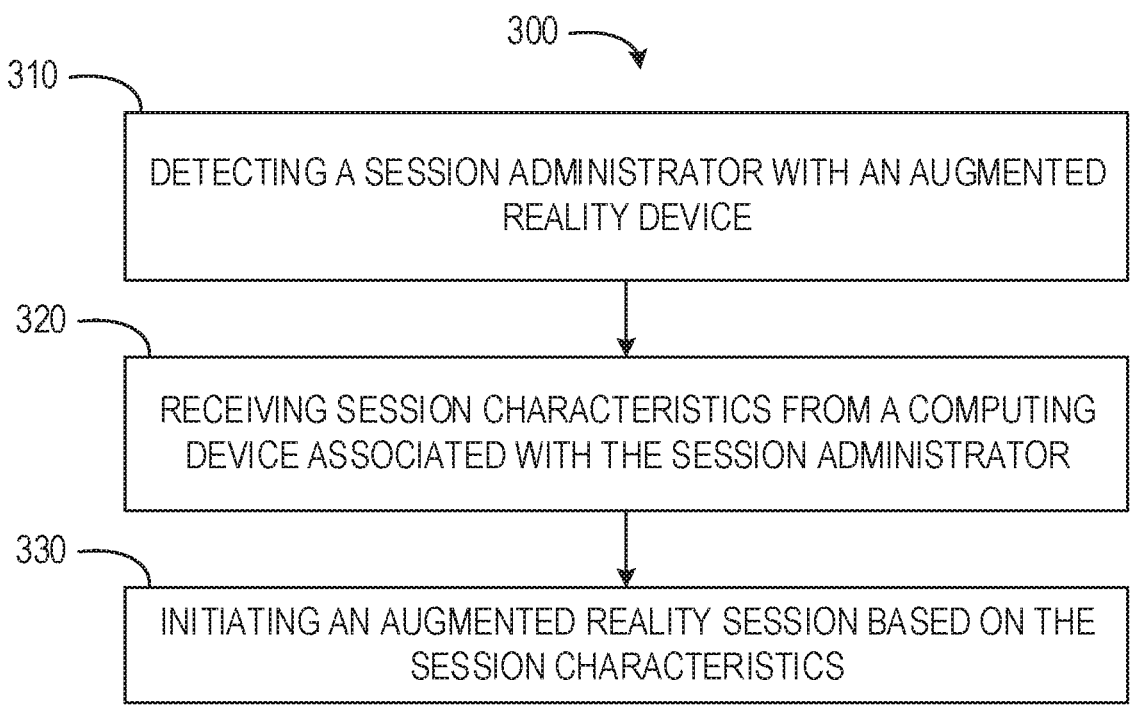
FIG. 3 depicts a flow diagram of a computer-implemented method for generating augmented reality sessions based on eye behavior of a user, according to at least one embodiment.

FIG. 3 shows a flow diagram of an embodiment of a computer-implemented method 300 for generating augmented reality sessions based on abnormal eye behavior of a user. The method 300 may be performed by or within the computing environment 100. In some embodiments, the method 300 comprises or incorporates one or more operations of the method 200. In some instances, operations of the method 300 may be incorporated as part of or sub-operations of the method 200.

In operation 310, the tracking component 110 detects a session administrator. The tracking component 110 may detect the session administrator using a second image capture device of the augmented reality device. For example, the tracking component 110 may use a rear-facing camera (e.g., the second image capture device) of the augmented reality device to detect the session administrator. In some embodiments, the tracking component 110 detects the session administrator during an initiation operation, prior to presentation of the augmented reality session. The detection of the session administrator may be performed prior to detection of the set of eye characteristics. In some embodiments, detection of the session administrator is performed during a setup procedure. The setup procedure may include connecting the augmented reality device to a computing device associated with the session administrator. The setup procedure may include presentation of and selection of the augmented reality session to be presented.

In operation 320, the session component 140 receives session characteristics from a computing device associated with the session administrator. The session component 140 may receive the session characteristics from the computing device in response to a portion of the setup procedure. In such instances, the session component 140 may receive the session characteristics in response to the session administrator selecting the augmented reality session to be presented. The session component 140 may also receive the session characteristics as a set of entries by the session administrator. The entries may comprise one or more selections for session goals, session tasks, session length, or any other suitable and relevant information describing the augmented reality session to be presented. In some instances, the session characteristics include a standard cognitive state for the user, a baseline set of eye characteristics for the user, a range of measurements or thresholds for eye characteristics of the user, or any other suitable and relevant information about the user of the augmented reality session.

In some embodiments, the session component 140 accesses the session characteristics. In such instances, the session component 140 may receive information about the user, such as an identifier. The session component 140 may also receive information about the session administrator. Based on the received information, the session component 140 may access a session repository. The session repository may contain information about historical sessions of the user, treatment plans, session or treatment goals, session or treatment activities, and any other suitable information. The session component 140 may retrieve the session characteristics from the session repository based on the received information.

In operation 330, the session component 140 cooperates with the presentation component 120 to initiate the augmented reality session. The augmented reality session is initiated in response to detecting the set of eye characteristics and receiving session characteristics from the computing device. In some embodiments, the augmented reality session may be initiated in a manner similar to or the same as described above with respect to operations 210-250.

Figure 4:
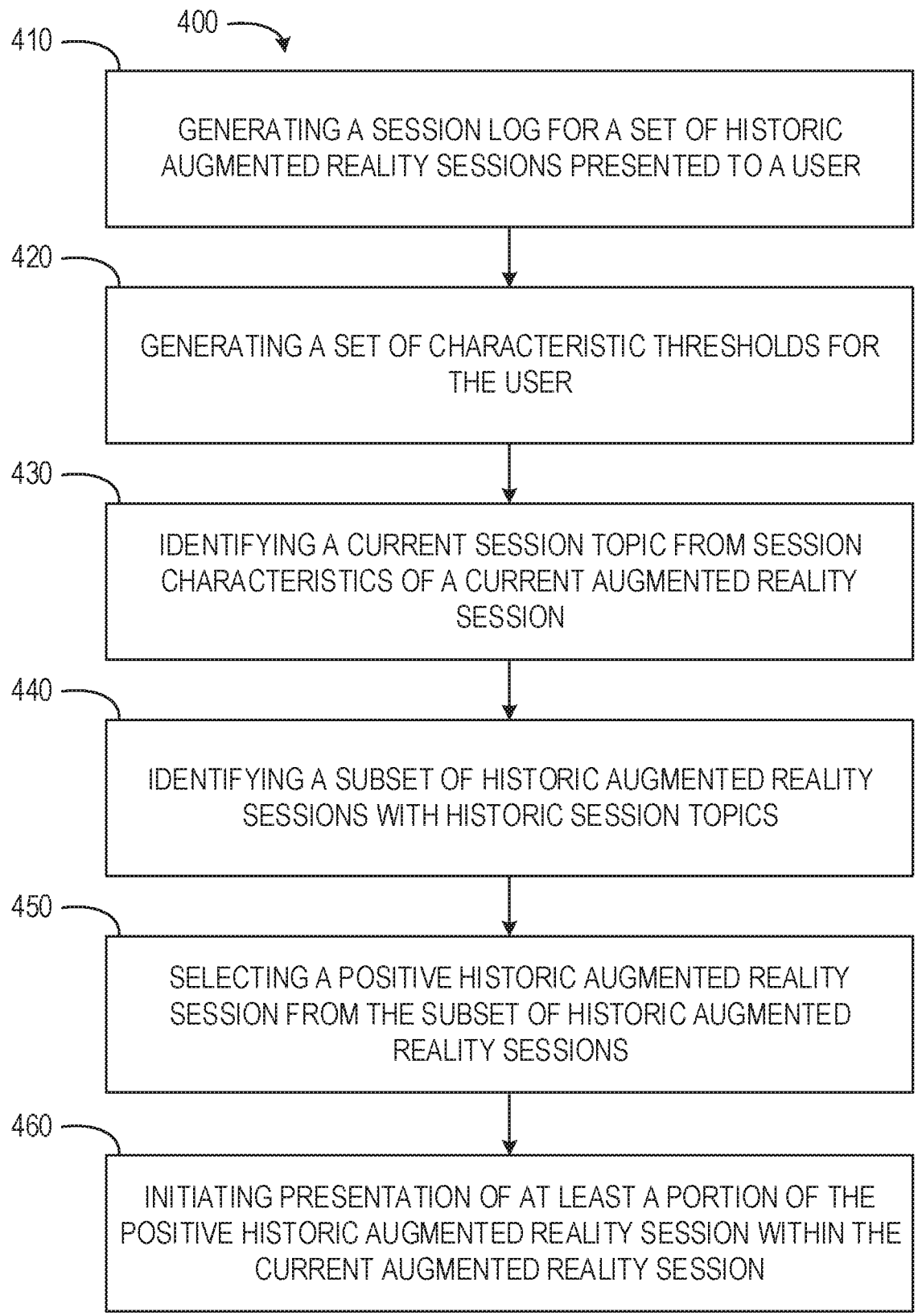
FIG. 4 depicts a flow diagram of a computer-implemented method for generating augmented reality sessions based on eye behavior of a user, according to at least one embodiment.

FIG. 4 shows a flow diagram of an embodiment of a computer-implemented method 400 for generating augmented reality sessions based on abnormal eye behavior of a user. The method 400 may be performed by or within the computing environment 100. In some embodiments, the method 400 comprises or incorporates one or more operations of the methods 200 or 300. In some instances, operations of the method 400 may be incorporated as part of or sub-operations of the methods 200 or 300. For example, at least a portion of the method 400 may be performed as part of operation 250 of the method 200.

In operation 410, the session component 140 generates a session log for a set of historic augmented reality sessions presented to a user. The session log includes a set of session characteristics and eye characteristics of the user. The set of session characteristics and the eye characteristics of the user may occur and be captured during each historic augmented reality session. The session log may be part of or stored in the session repository. In some embodiments, an augmented reality session is added to the session log upon completion of the augmented reality session. In some instances, each time the user engages in an augmented reality session, the augmented reality session is added to the session log. In such instances, success or failure of a session may be logged along with the information about the session within the session log.

In operation 420, the session component 140 generates a set of characteristic thresholds for the user. The set of characteristic thresholds may be generated based on the eye characteristics of the user occurring during the set of historic augmented reality sessions. In some embodiments, the set of characteristic thresholds are generated in a manner similar to or the same as described above with respect to operations 210 and 240. The session component 140 may generate the set of characteristic thresholds based on ranges of eye location and eye movement for the user.

In some embodiments, the session component 140 incorporates feedback from a session administrator. In such instances, the session administrator, in a previous augmented reality session, may indicate a cognition point at which the cognitive state or attentiveness of the user began to decline or declined past an acceptable level. The session component 140 may identify the cognition point of a plurality of historic augmented reality sessions for the user. The session component 140 may determine eye movement measurements and eye location measurements for a subset of frames preceding and following the cognition point. The session component 140 may determine a difference between the set of eye characteristics or a baseline for the set of eye characteristics for the user, indicating a starting point for eye characteristics of a user at a beginning of one or more augmented reality sessions. The session component 140 may generate the set of characteristic thresholds as one or more of an average measurement of eye movement and eye location for two or more cognition points and an average difference between eye measurements at the cognition points and the baseline for the set of eye characteristics.

In operation 430, the session component 140 identifies a current session topic from session characteristics of the current augmented reality session. The current session topic may be stored within the session logs, the session repository, or session metadata. In some embodiments, the session component 140 identifies the current session topic in response to the state component 130 determining the change in the at least one eye characteristic in operation 240. The session component 140 may also identify the current session topic after initiation of the augmented reality session in operation 220.

In operation 440, the session component 140 identifies a subset of historic augmented reality sessions with historic session topics. The subset of historic augmented reality sessions may be identified from the session log. The historic session topics may match the current session topic. In some embodiments, the session component 140 identifies the subset of historic augmented reality sessions based on identifying the session topic. In some embodiments, the session component 140 identifies the subset of historic augmented reality sessions with historic session topics matching the current session topic in response to the change in the at least one eye characteristic being determined in operation 240 and the current session topic being identified in operation 430.

In operation 450, the session component 140 selects a positive historic augmented reality session from the subset of historic augmented reality sessions. The positive historic augmented reality session is associated with a cognitive state greater than the reduced cognitive state. In some embodiments, the positive historic augmented reality session is associated with a successful outcome or most successful augmented reality session. The session component 140 may select the positive historic augmented reality session by querying the session log or the session repository. The session component 140 may determine the positive historic augmented reality session as a historic augmented reality session associated with a topic matching the current session topic and having a cognitive state above a specified cognitive state. In some embodiments, the session component 140 may determine the matching session topic and the specified cognitive state based on metadata, session data, or session administrator comments within the session log or the session repository.

In operation 460, the presentation component 120 initiates presentation of at least a portion of the positive historic augmented reality session within the current augmented reality session. The presentation component 120 may present, within the current augmented reality session, one or more audio elements, visual elements, themes, or other session characteristics from the positive historic augmented reality session. In some embodiments, the presentation component 120 incorporates one or more of an audio overlay or a video overlay into the current augmented reality session. For example, where a user with a lowered cognitive state is engaged in an augmented reality session with a therapy task of working with "R" sounds and the augmented reality system 102 determines the cognitive state of the user is decreasing, the presentation component 120 may initiate presentation of audio/visual elements recorded from previous sessions where the session resulted in a higher cognitive state. For example, the presentation component 120 may incorporate audio and visual elements from a different session administrator and a historic session having a session topic relating to working with "R" sounds.

Figure 5:
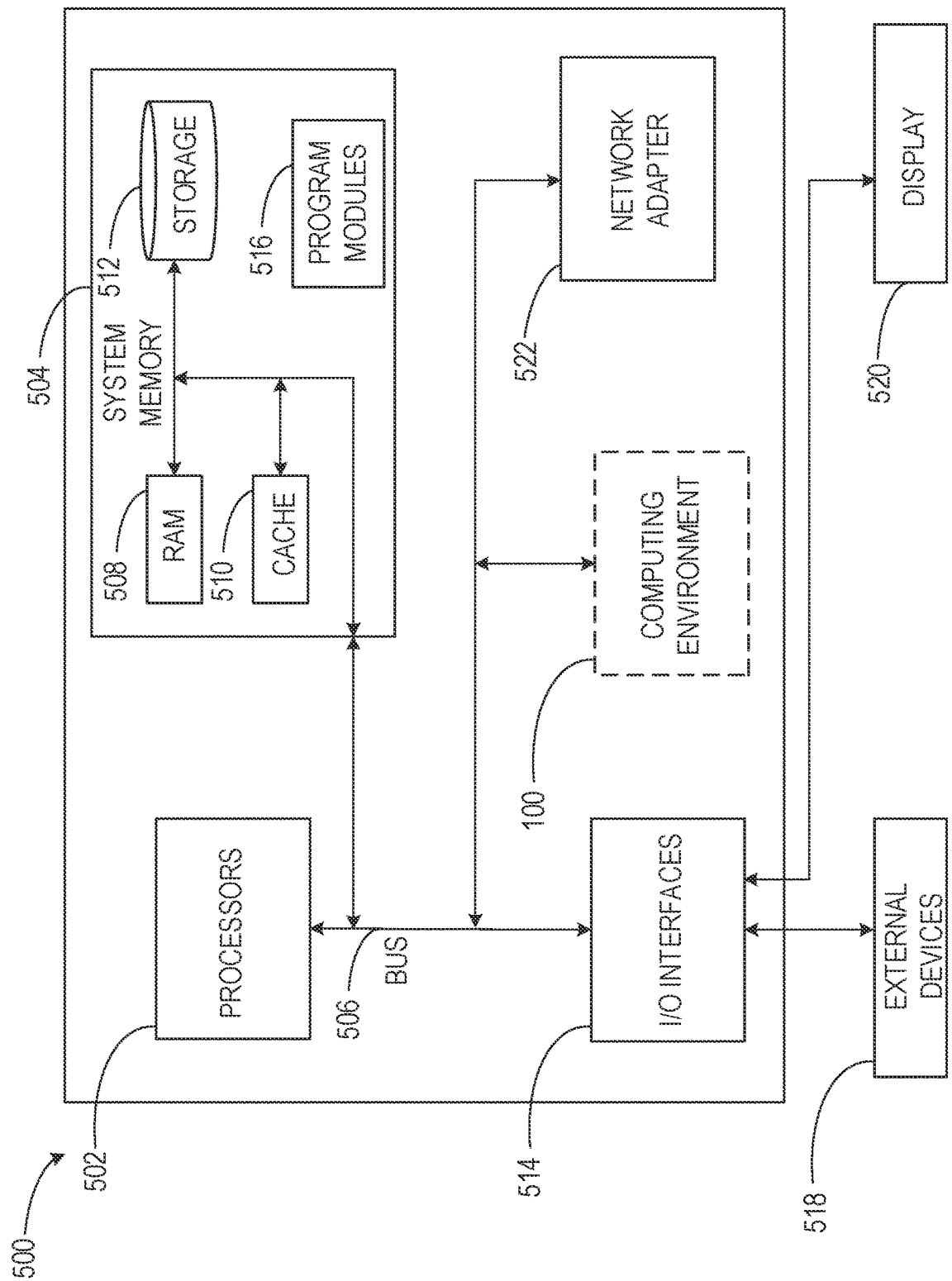
FIG. 5 depicts a block diagram of a computing system for generating augmented reality sessions based on eye behavior of a user, according to at least one embodiment.

Embodiments of the present disclosure may be implemented together with virtually any type of computer, regardless of the platform being suitable for storing and/or executing program code. FIG. 5 shows, as an example, a computing system 500 (e.g., cloud computing system) suitable for executing program code related to the methods disclosed herein and for generating augmented reality sessions based on abnormal eye behavior of a user.

The computing system 500 is only one example of a suitable computer system and is not intended to suggest any limitation as to the scope of use or functionality of embodiments of the present disclosure described herein, regardless, whether the computer system 500 is capable of being implemented and/or performing any of the functionality set forth hereinabove. In the computer system 500, there are components, which are operational with numerous other general purpose or special purpose computing system environments or configurations. Examples of well-known computing systems, environments, and/or configurations that may be suitable for use with computer system/server 500 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Computer system/server 500 may be described in the general context of computer system-executable instructions, such as program modules, being executed by a computer system 500. Generally, program modules may include routines, programs, objects, components, logic, data structures, and so on that perform particular tasks or implement particular abstract data types. Computer system/server 500 may be practiced in distributed cloud computing environments where tasks are performed by remote processing devices that are linked through a communications network. In a distributed cloud computing environment, program modules may be located in both, local and remote computer system storage media, including memory storage devices.

As shown in the figure, computer system/server 500 is shown in the form of a general-purpose computing device. The components of computer system/server 500 may include, but are not limited to, one or more processors 502 (e.g., processing units), a system memory 504 (e.g., a computer-readable storage medium coupled to the one or more processors), and a bus 506 that couple various system components including system memory 504 to the processor 502. Bus 506 represents one or more of any of several types of bus structures, including a memory bus or memory controller, a peripheral bus, an accelerated graphics port, and a processor or local bus using any of a variety of bus architectures. By way of example, and not limiting, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/server 500 typically includes a variety of computer system readable media. Such media may be any available media that is accessible by computer system/server 500, and it includes both, volatile and non-volatile media, removable and non-removable media.

The system memory 504 may include computer system readable media in the form of volatile memory, such as random-access memory (RAM) 508 and/or cache memory 510. Computer system/server 500 may further include other removable/non-removable, volatile/non-volatile computer system storage media. By way of example only, a storage system 512 may be provided for reading from and writing to a non-removable, non-volatile magnetic media (not shown and typically called a 'hard drive'). Although not shown, a magnetic disk drive for reading from and writing to a removable, non-volatile magnetic disk (e.g., a 'floppy disk'), and an optical disk drive for reading from or writing to a removable, non-volatile optical disk such as a CD-ROM, DVD-ROM or other optical media may be provided. In such instances, each can be connected to bus 506 by one or more data media interfaces. As will be further depicted and described below, the system memory 504 may include at least one program product having a set (e.g., at least one) of program modules that are configured to carry out the functions of embodiments of the present disclosure.

The program/utility, having a set (at least one) of program modules 516, may be stored in the system memory 504 by way of example, and not limiting, as well as an operating system, one or more application programs, other program modules, and program data. Program modules may include one or more of the tracking component 110, the presentation component 120, the state component 130, and the session component 140, which are illustrated in FIG. 1. Each of the operating systems, one or more application programs, other program modules, and program data or some combination thereof, may include an implementation of a networking environment. Program modules 516 generally carry out the functions and/or methodologies of embodiments of the present disclosure, as described herein.

The computer system/server 500 may also communicate with one or more external devices 518 such as a keyboard, a pointing device, a display 520, etc.; one or more devices that enable a user to interact with computer system/server 500; and/or any devices (e.g., network card, modem, etc.) that enable computer system/server 500 to communicate with one or more other computing devices. Such communication can occur via Input/Output (I/O) interfaces 514. Still yet, computer system/server 500 may communicate with one or more networks such as a local area network (LAN), a general wide area network (WAN), and/or a public network (e.g., the Internet) via network adapter 522. As depicted, network adapter 522 may communicate with the other components of computer system/server 500 via bus 506. It should be understood that, although not shown, other hardware and/or software components could be used in conjunction with computer system/server 500. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Service models may include software as a service (SaaS), platform as a service (PaaS), and infrastructure as a service (IaaS). In SaaS, the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings. In PaaS, the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. In IaaS, the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment models may include private cloud, community cloud, public cloud, and hybrid cloud. In private cloud, the cloud infrastructure is operated solely for an organization. It may be managed by the organization or a third party and may exist on-premises or off-premises. In community cloud, the cloud infrastructure is shared by several organizations and supports specific community that has shared concerns (e.g., mission, security requirements, policy, and compliance considerations). It may be managed by the organizations or a third party that may exist on-premises or off-premises. In public cloud, the cloud infrastructure is made available to the general public or a large industry group and is owned by an organization selling cloud services. In hybrid cloud, the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling modularity, and semantic interoperability. At the heart of cloud computing is an infrastructure that includes a network of interconnected nodes.

Figure 6:
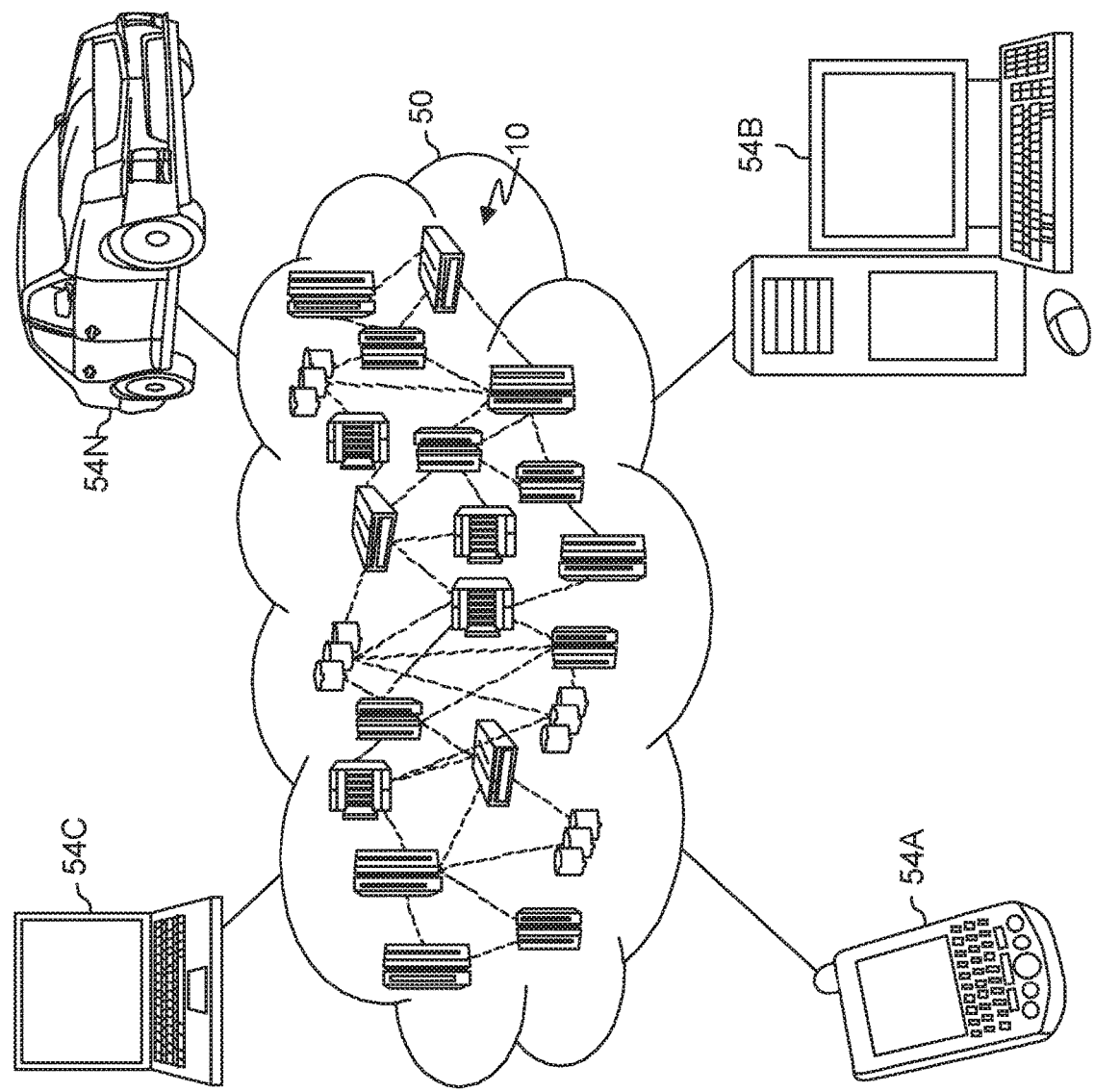
FIG. 6 is a schematic diagram of a cloud computing environment in which concepts of the present disclosure may be implemented, in accordance with an embodiment of the present disclosure.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 7:
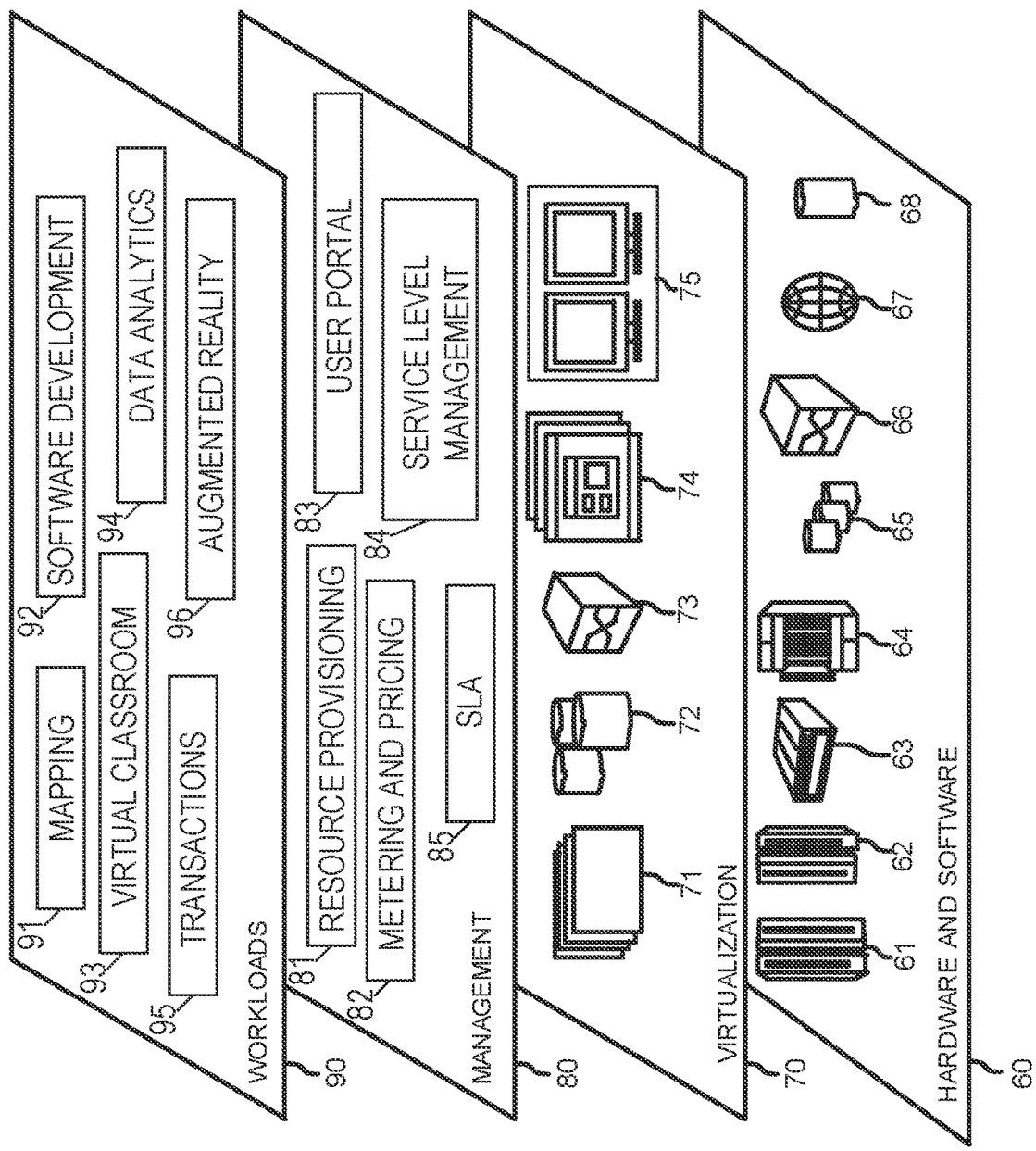
FIG. 7 is a diagram of model layers of a cloud computing environment in which concepts of the present disclosure may be implemented, in accordance with an embodiment of the present disclosure.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and augmented reality processing 96.

Cloud models may include characteristics including on-demand self-service, broad network access, resource pooling, rapid elasticity, and measured service. In on-demand self-service a cloud consumer may unilaterally provision computing capabilities such as server time and network storage, as needed automatically without requiring human interaction with the service's provider. In broad network access, capabilities are available over a network and accessed through standard mechanisms that promote use by heterogeneous thin or thick client platforms (e.g., mobile phones, laptops, and PDAs). In resource pooling, the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). In rapid elasticity, capabilities can be rapidly and elastically provisioned, in some cases automatically, to quickly scale out and rapidly released to quickly scale in. To the consumer, the capabilities available for provisioning often appear to be unlimited and can be purchased in any quantity at any time. In measured service, cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

The descriptions of the various embodiments of the present disclosure have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer-readable storage medium (or media) having computer readable program instructions thereon for causing a processor to carry out aspects of the present invention.

The computer-readable storage medium may be an electronic, magnetic, optical, electromagnetic, infrared or a semi-conductor system for a propagation medium. Examples of a computer-readable medium may include a semi-conductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W), DVD and Blu-Ray-Disk.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer-readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatuses, or another device to cause a series of operational steps to be performed on the computer, other programmable apparatus or other device to produce a computer implemented process, such that the instructions which execute on the computer, other programmable apparatuses, or another device implement the functions/acts specified in the flowchart and/or block diagram block or blocks.

The flowcharts and/or block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The terminology used herein is for the purpose of describing particular embodiments only and is not intended to limit the present disclosure. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present disclosure has been presented for purposes of illustration and description, but is not intended to be exhaustive or limited to the present disclosure in the form disclosed. Many modifications and variations will be apparent to those of ordinary skills in the art without departing from the scope of the present disclosure. The embodiments are chosen and described in order to explain the principles of the present disclosure and the practical application, and to enable others of ordinary skills in the art to understand the present disclosure for various embodiments with various modifications, as are suited to the particular use contemplated.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   detecting, using an image capture device of an augmented reality device, a set of eye characteristics of a user;
   generating a session log for a set of historic augmented reality sessions presented to the user, the session log including a set of session characteristics and eye characteristics of the user occurring during each historic augmented reality session;
   based on the eye characteristics of the user occurring during the set of historic augmented reality sessions, generating a set of characteristic thresholds for the user;
   in response to detecting the set of eye characteristics, initiating presentation of an augmented reality session using the augmented reality device;
   detecting a change to at least one eye characteristic of the set of eye characteristics of the user;
   in response to detecting the change and based on the set of characteristic thresholds for the user, determining the change to the at least one eye characteristic indicates a reduced cognitive state of the user; and
   in response to determining the change indicates the reduced cognitive state, modifying the augmented reality session being presented to the user.

2. The computer-implemented method of claim 1, wherein the image capture device of the augmented reality device is a first image capture device, the method further comprising:
   detecting, using a second image capture device of the augmented reality device, a session administrator;
   receiving session characteristics from a computing device associated with the session administrator; and
   wherein the augmented reality session is initiated in response to detecting the set of eye characteristics and receiving session characteristics from the computing device.

3. The computer-implemented method of claim 1, wherein determining the change indicates the reduced cognitive state further comprises:
   determining a standard cognitive state for the user, the standard cognitive state associated with a set of characteristic thresholds of the user;
   in response to detecting the change to the at least one eye characteristic, accessing the standard cognitive state for the user; and
   determining the change to the at least one eye characteristic exceeds a characteristic threshold of the set of characteristic thresholds.

4. The computer-implemented method of claim 1, wherein the augmented reality session is a current augmented reality session, and wherein modifying the augmented reality session further comprises:
   identifying a current session topic from session characteristics of the current augmented reality session;
   based on identifying the session topic, identifying, from the session log, a subset of historic augmented reality sessions with historic session topics matching the session topic;

selecting a positive historic augmented reality session from the subset of historic augmented reality sessions, the positive historic augmented reality session being associated with a cognitive state greater than the reduced cognitive state; and initiating presentation of at least a portion of the positive historic augmented reality session within the current augmented reality session.

5. The computer-implemented method of claim 1, further comprising:

in response to completing the augmented reality session, storing session characteristics of the augmented reality session and eye characteristics of the user in the session log.

6. A system, comprising:

one or more processors; and a computer-readable storage medium, coupled to the one or more processors, storing program instructions that, when executed by the one or more processors, cause the one or more processors to perform operations comprising:

detecting, using an image capture device of an augmented reality device, a set of eye characteristics of a user;

generating a session log for a set of historic augmented reality sessions presented to the user, the session log including a set of session characteristics and eye characteristics of the user occurring during each historic augmented reality session;

based on the eye characteristics of the user occurring during the set of historic augmented reality sessions, generating a set of characteristic thresholds for the user;

in response to detecting the set of eye characteristics, initiating presentation of an augmented reality session using the augmented reality device;

detecting a change to at least one eye characteristic of the set of eye characteristics of the user;

in response to detecting the change and based on the set of characteristic thresholds for the user, determining the change to the at least one eye characteristic indicates a reduced cognitive state of the user; and in response to determining the change indicates the reduced cognitive state, modifying the augmented reality session being presented to the user.

7. The system of claim 6, wherein the image capture device of the augmented reality device is a first image capture device, the operations further comprise:

detecting, using a second image capture device of the augmented reality device, a session administrator;

receiving session characteristics from a computing device associated with the session administrator; and wherein the augmented reality session is initiated in response to detecting the set of eye characteristics and receiving session characteristics from the computing device.

8. The system of claim 6, wherein determining the change indicates the reduced cognitive state further comprises:

determining a standard cognitive state for the user, the standard cognitive state associated with a set of characteristic thresholds of the user;

in response to detecting the change to the at least one eye characteristic, accessing the standard cognitive state for the user; and determining the change to the at least one eye characteristic exceeds a characteristic threshold of the set of characteristic thresholds.

9. The system of claim 6, wherein the augmented reality session is a current augmented reality session, and wherein modifying the augmented reality session further comprises:

identifying a current session topic from session characteristics of the current augmented reality session;

based on identifying the session topic, identifying, from the session log, a subset of historic augmented reality sessions with historic session topics matching the session topic;

selecting a positive historic augmented reality session from the subset of historic augmented reality sessions, the positive historic augmented reality session being associated with a cognitive state greater than the reduced cognitive state; and initiating presentation of at least a portion of the positive historic augmented reality session within the current augmented reality session.

10. The system of claim 6, wherein the operations further comprise:

in response to completing the augmented reality session, storing session characteristics of the augmented reality session and eye characteristics of the user in the session log.

11. A computer program product comprising a computer readable storage medium having program instructions embodied therewith, the program instructions being executable by one or more processors to cause the one or more processors to perform operations comprising:

detecting, using an image capture device of an augmented reality device, a set of eye characteristics of a user;

generating a session log for a set of historic augmented reality sessions presented to the user, the session log including a set of session characteristics and eye characteristics of the user occurring during each historic augmented reality session;

based on the eye characteristics of the user occurring during the set of historic augmented reality sessions, generating a set of characteristic thresholds for the user;

in response to detecting the set of eye characteristics, initiating presentation of an augmented reality session using the augmented reality device;

detecting a change to at least one eye characteristic of the set of eye characteristics of the user;

in response to detecting the change and based on the set of characteristic thresholds for the user, determining the change to the at least one eye characteristic indicates a reduced cognitive state of the user; and in response to determining the change indicates the reduced cognitive state, modifying the augmented reality session being presented to the user.

12. The computer program product of claim 11, wherein the image capture device of the augmented reality device is a first image capture device, the operations further comprise:

detecting, using a second image capture device of the augmented reality device, a session administrator;

receiving session characteristics from a computing device associated with the session administrator; and wherein the augmented reality session is initiated in response to detecting the set of eye characteristics and receiving session characteristics from the computing device.

13. The computer program product of claim 11, wherein determining the change indicates the reduced cognitive state further comprises:

determining a standard cognitive state for the user, the standard cognitive state associated with a set of characteristic thresholds of the user;

in response to detecting the change to the at least one eye characteristic, accessing the standard cognitive state for the user; and determining the change to the at least one eye characteristic exceeds a characteristic threshold of the set of characteristic thresholds.

14. The computer program product of claim 11, wherein the augmented reality session is a current augmented reality session, and wherein modifying the augmented reality session further comprises:

identifying a current session topic from session characteristics of the current augmented reality session;

based on identifying the session topic, identifying, from the session log, a subset of historic augmented reality sessions with historic session topics matching the session topic;

selecting a positive historic augmented reality session from the subset of historic augmented reality sessions, the positive historic augmented reality session being associated with a cognitive state greater than the reduced cognitive state; and initiating presentation of at least a portion of the positive historic augmented reality session within the current augmented reality session.

* * * * *